United States Patent [19]

Wright et al.

[11] Patent Number: 4,569,827

[45] Date of Patent: Feb. 11, 1986

[54] MULTISTAGE SYSTEM FOR PRODUCING HYDROCARBONS

[75] Inventors: Bernard S. Wright, East Windsor; Hartley Owen, Belle Mead; Chung H. Hsia, Matawan, all of N.J.

[73] Assignee: Mobil Oil Corporation, New York, N.Y.

[21] Appl. No.: 669,927

[22] Filed: Nov. 9, 1984

Related U.S. Application Data

[62] Division of Ser. No. 598,955, Apr. 11, 1984, Pat. No. 4,497,968.

[51] Int. Cl.[4] ............................................. B01J 8/04
[52] U.S. Cl. ........................................ 422/190; 208/49
[58] Field of Search ............... 585/304, 413, 330, 489, 585/415, 640, 322, 407, 319, 533, 517, 315, 314, 254, 255, 639; 208/138, 71, 341, 149, 255, 135; 55/48; 422/116, 190, 189, 142, 141, 201; 196/46

[56] References Cited

U.S. PATENT DOCUMENTS

| | | | |
|---|---|---|---|
| 3,421,610 | 1/1969 | Marshall | 208/341 X |
| 3,470,084 | 9/1969 | Scott | 208/341 X |
| 3,537,978 | 11/1970 | Borst, Jr. | 208/341 X |
| 3,607,734 | 9/1971 | Stafford, Sr. | 208/341 |
| 4,309,272 | 1/1982 | Johnson et al. | 585/330 X |
| 4,433,185 | 2/1984 | Tabak | 585/415 X |
| 4,450,311 | 5/1984 | Wright et al. | 585/413 |
| 4,456,779 | 6/1984 | Owen et al. | 585/415 |
| 4,479,812 | 10/1984 | Hsia et al. | 55/48 |

Primary Examiner—Richard L. Chiesa
Attorney, Agent, or Firm—A. J. McKillop; M. G. Gilman; L. G. Wise

[57] ABSTRACT

A multistage technique for converting olefins to heavier hydrocarbons including a sorption prefractionation unit for separating olefinic feedstock into a sorbate stream rich in liquified olefins and a vapor stream rich in light olefins; a first stage catalytic reactor unit for oligomerizing olefins from the sorbate stream including means for maintaining the first stage at elevated pressure and predetermined temperature for producing substantially linear aliphatic hydrocarbons; a second stage catalytic reactor unit for oligomerizing light olefin including means for maintaining the second stage under high severity conditions at substantially higher temperature than the first stage; and a product fractionation unit for separating effluent from the first and second stages to separate and recover heavy hydrocarbon product and a sorbent recycle fraction. The sorbent fraction is recycled to the sorption prefractionation unit for contacting olefinic feedstock with the recycled sorbent. Unconverted second stage olefins may be also sorbed by the recycled fraction for further reaction.

7 Claims, 5 Drawing Figures

MULTISTAGE SYSTEM FOR PRODUCING HYDROCARBONS

This is a divisional of copending application Ser. No. 598,955, filed on Apr. 11, 1984 and now U.S. Pat. No. 4,497,968.

FIELD OF THE INVENTION

This invention relates to a system for converting light olefins or organic oxygenate precursors, such as methanol or dimethyl ether (DME), to liquid hydrocarbons. In particular it provides a continuous process for producing distillate range fuel products by oligomerizing fractionated olefins to produce a major amount of distillate product for use as diesel fuel or the like.

BACKGROUND OF THE INVENTION

Recent developments in zeolite catalysts and hydrocarbon conversion processes have created interest in utilizing olefinic feedstocks, for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$–$C_5$ alkenes. This process may supplant conventional alkylation units. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Olefinic gasoline can be produced in good yield by the MOGD process and may be recovered as a product or recycled to the reactor system for further conversion to distillate-range products. Distillate mode operation can be employed to maximize production of $C_{10}+$ aliphatics by reacting the lower olefins at high pressure and moderate temperature. Operating details for typical MOGD units are disclosed in copending U.S. patent applications Ser No. 488,834, filed Apr. 26, 1983 (Owen et al) now U.S. Pat. No. 4,456,779 and Ser. No. 481,705, filed Apr. 4, 1983 (Tabak) now U.S. Pat. No. 4,433,185, incorporated herein by reference.

In addition to their use as shape selective oligomerization catalysts, the medium pore ZSM-5 type catalysts are useful for converting methanol and other lower aliphatic alcohols and/or corresponding ethers to olefins. Particular interest has been directed to a catalytic process for converting low cost methanol to valuable hydrocarbons rich in ethene and $C_3+$ alkenes. Various processes are described in U.S. Pat. Nos. 3,894,107 (Butter et al), 3,928,483 (Chang et al), 4,025,571 (Lago), and in copending U.S. patent application Ser. No. 388,768, filed June 15, 1982 (Yurchak et al) and now abandoned. Significance of the methanol-to-olefins ("MTO") type processes, especially for producing ethene, is discusssed in *Hydrocarbon Processing*, November 1982, pp. 117-120. It is generally known that the MTO process can be optimized to produce a major fraction of $C_2$–$C_4$ olefins.

SUMMARY OF THE INVENTION

A continuous catalytic process has been found for converting olefinic feedstock comprising ethylene and $C_3+$ olefins to heavier liquid hydrocarbon product. Methods and means are provided for prefractionating the olefinic feedstock to obtain a gaseous stream rich in ethylene and a liquid stream containing $C_3+$ olefin; heating and contacting the liquid stream from the prefractionating step with shape selective medium pore zeolite oligomerization catalyst in a distillate mode catalytic reactor system at elevated temperature and pressure to provide a heavier hydrocarbon effluent stream comprising distillate, gasoline and lighter hydrocarbons; fractionating the effluent stream to recover distillate, gasoline and lighter hydrocarbons; recycling at least a portion of the recovered gasoline as a first liquid sorbent stream to the prefractionating step; further reacting the recycled gasoline together with sorbed $C_3+$ olefin in the distillate mode catalytic reactor system; combining the ethylene-rich gaseous stream with a liquid hydrocarbon stream containing heavier liquid hydrocarbons; contacting the combined high severity reaction zone with shape selective medium pore zeolite oligomerization catalyst to convert at least a portion of the olefinic components to heavier hydrocarbons; cooling oligomerization reaction effluent from the high severity reaction zone to condense at least a portion of the heavier hydrocarbons; separating the cooled and partially condensed high severity reactor effluent stream into a vapor stream comprising unreacted light olefin and a condensed liquid hydrocarbon stream; fractionating the condensed liquid hydrocarbons from the high severity reaction effluent to provide a recycle sorbent stream and at least one product hydrocarbon stream; contacting the vapor stream from the high severity reaction effluent under sorption pressure conditions with cooled recycle sorbent stream to sorb said unreacted light olefin into the sorbent stream; and recycling the sorbent stream rich in olefin for further conversion with the olefinic feedstock. Advantageously, the first and second sorbent streams are recovered in a common fractination unit.

The oligomerization catalyst preferably comprises ZSM-5 type zeolite. Other objects and features of the invention will be seen in the following description and drawings.

THE DRAWINGS

DESCRIPTION OF PREFERRED EMBODIMENTS

Catalyst versatility permits the same zeolite to be used in both the distillate mode primary stage and high severity secondary oligomerization stage. While it is within the inventive concept to employ substantially different catalysts in these stages, it is advantageous to employ a standard ZSM-5 having a silica alumina molar ratio of 70:1.

The oligomerization catalysts preferred for use herein include the medium pore shape selective crystalline aluminosilicate zeolites having a silica to alumina ratio of at least 12, a constraint index of about 1 to 12 and acid cracking activity of about 160-200. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449, 4,076,979, 3,832,449, 4,076,842, 4,016,245 and 4,046,839, 4,414,423 and 4,417,086-8. The disclosures of these patents are incorporated herein by reference. A suitable catalyst for each fixed bed operation consisting essentially of HZSM-5 zeolite with 35 wt. % alumina binder in the form of cylindrical extrudates of about 1-5 mm diameter. Other catalysts which may be employed for converting methanol/DME to lower olefins and oligomerizing same include the borosilicate, ferrosilicate, "silicalite" and/or synthetic mordenite materials.

In this description, metric units and parts by weight are employed unless otherwise stated. While various reactor configurations may be used, including fluidized bed catalytic reactors, moving bed and fixed bed reactors, the invention is described for use in a plurality of fixed bed reactors operated under differing process conditions depending upon relative position in the system.

Figure 1:
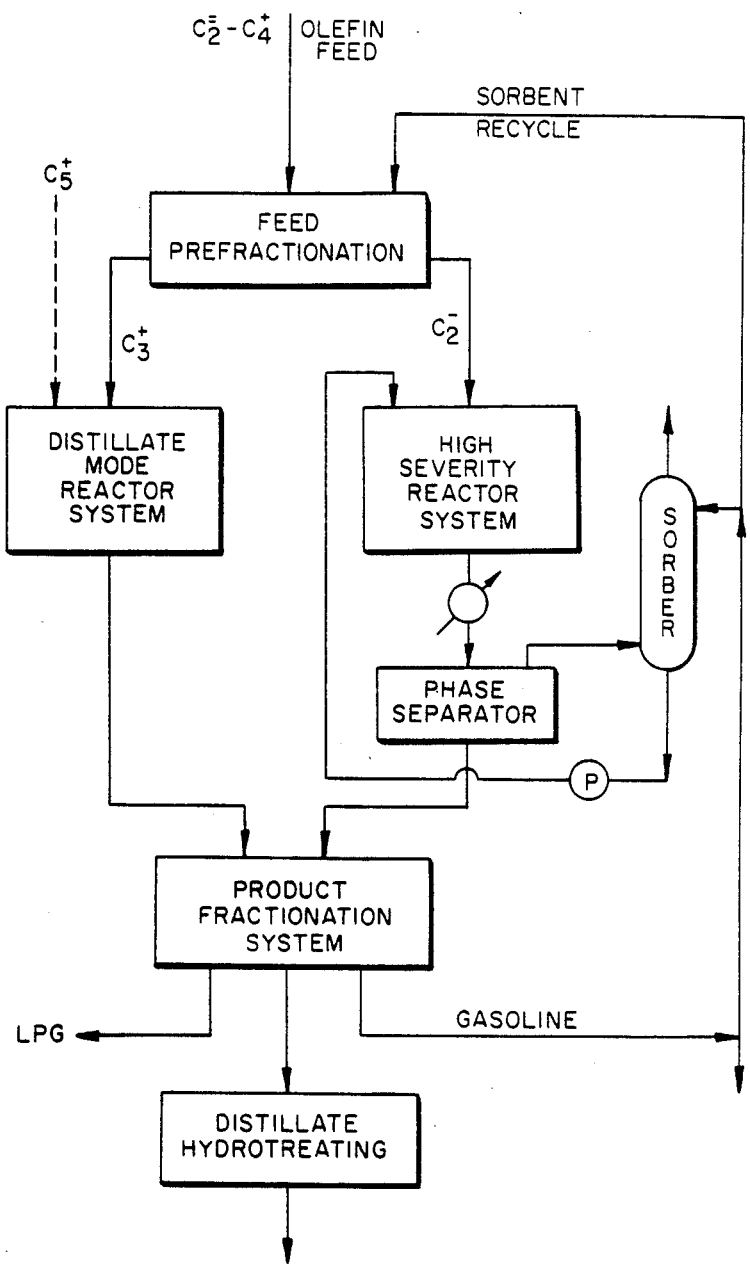
FIG. 1 is a process flow sheet showing the major unit operations and process streams.

Referring to FIG. 1, olefinic feedstock is contacted with a gasoline sorbent stream in a prefractionation section to provide a $C_3+$ liquid stream, which is passed to the distillate mode oligomerization reactor system. The combined olefinic stream (containing recycled olefinic gasoline rich in $C_3$–$C_4$ olefin sorbate) is reacted at high pressure and elevated temperature over the oligomerization catalyst. Distillate-rich effluent is then passed to a product fractionation system and separated into light gases (LPG), $C_5+$ gasoline for recycle and distillate range hydrocarbons. The distillate stream contains a major amount of high boiling aliphatics, such as $C_{10}$–$C_{20}$ hydrocarbons, and a minor amount of aromatics. The distillate product may be further stabilized by hydrotreating (HDT) in a relatively mild process to saturate the olefinic compounds and convert aromatics to corresponding naphthenes without substantial cracking or dealkylation to yield a distillate fuel product. Ethylene (ethene, $C_2H_2$) recovered from the prefractionator is converted in a high severity reactor system, the effluent from which is cooled to condense $C_5+$ hydrocarbons for further fractionation. For this purpose the condensed effluent from the high severity reactor may be combined with the distillate-rich stream. Unconverted vapor effluent may be recovered by absorption in a liquid sorbent, such as recycled gasoline, and further reacted in the high severity reactor. Since the recycled streams are liquid, they may be repressurized at moderate cost by pumping.

Figure 2:
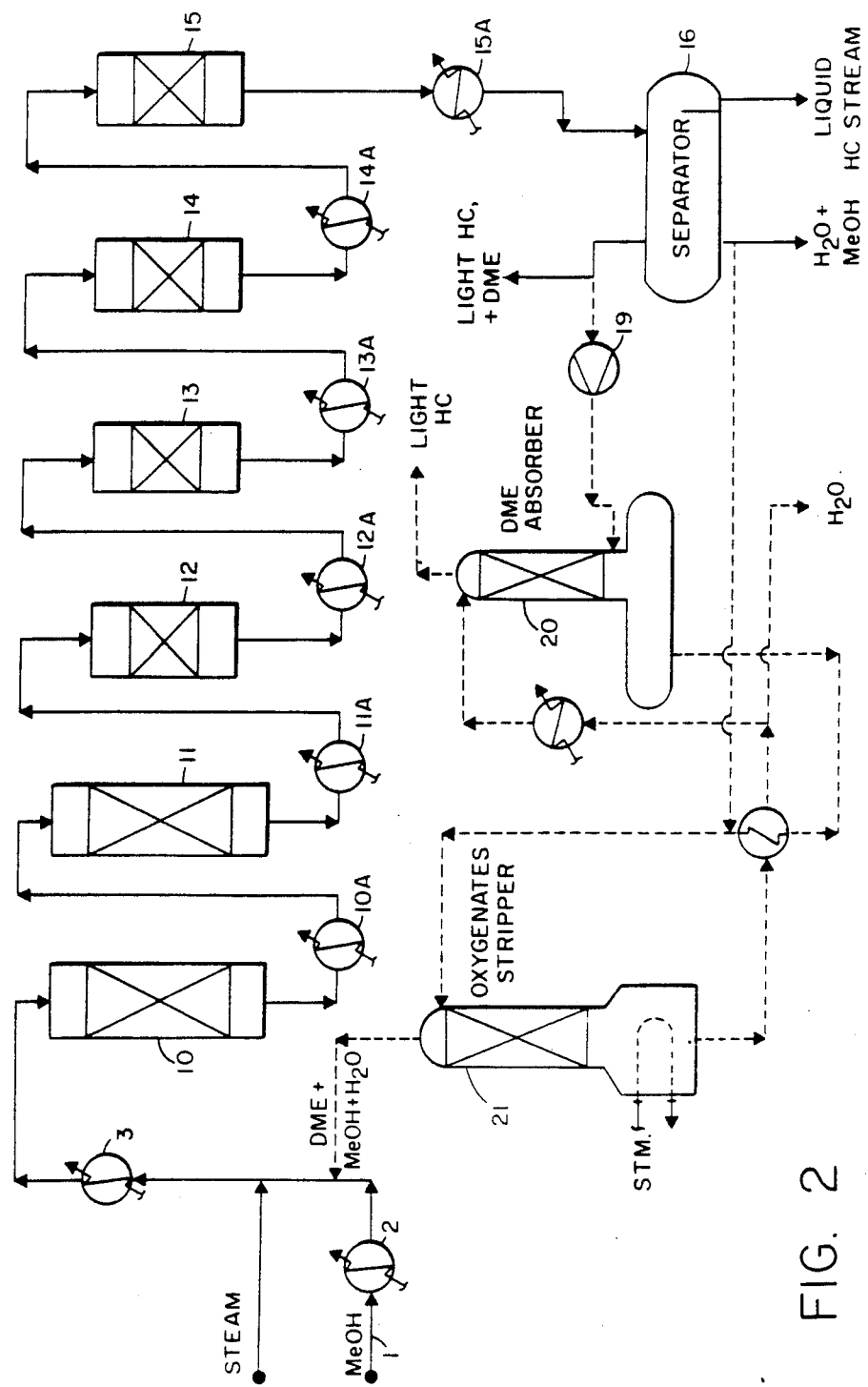
FIG. 2 is a schematic representation of a preferred multi-reactor system and fractionation system for dehydration and conversion of methanol and/or DME to lower olefins.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the distillate mode conditions do not convert a major fraction of ethylene. While propene, butene-1 and others may be converted to the extent of 50 to 95% in the distillate mode, only about 10 to 50% of the ethylene component will be consumed. Accordingly, the ethene is advantageously recovered prior to the oligomerization stage. In a preferred embodiment the olefinic feedstock is obtained from lower aliphatic oxygenates, such as methanol or dimethylether (DME). FIG. 2 depicts a fixed bed multi-reactor (MTO) system for converting methanol ($CH_3OH$) and/or DME. A typical crude methanol feedstock may contain 4 to 17% water, with minor amounts of carbon oxides, methane, DME, etc.

In the oxygenate conversion stage, ethene production may be optimized by employing fixed bed primary stage conditions in the temperature range of about 260° C. to 425° C., a pressure range of about 170 to 800 kPa and weight hourly space velocity range of about 0.5 to 1.0 based on ZSM-5 equivalent catalyst and methanol equivalent in the primary stage feedstock. Typically about 25 to 90% of oxygenate feed is converted per reactor pass and water diluent is cofed with methanol and/or dimethyl ether in a molar ratio of about 0.1:1 to 5:1. Under these conditions, the primary stage hydrocarbon effluent usually contains about 25 to 40 wt. % ethene, about 10 to 50 wt. % propene, about 2 to 30 wt. % butene, less than 10 wt. % $C_1$ to $C_4$ paraffins, and about 5 to 20 wt. % aromatics, including about 1 to 5 wt. % durene.

In the embodiment of FIG. 2, the feedstock is methanol (MeOH), which may be partially dehydrated in a separate process step over gamma-alumina catalyst to yield dimethyl ether (DME) and water. A preliminary dewatering step can be used to provide a feedstock consisting essentially of MeOH and/or DME; however, the presence of water in the MTO reactor may be beneficial. The oxygenate is fed continuously under low pressure through line 1 and heat exchanger 2, where it is raised to process temperature, and introduced to the first stage MTO reactor system. The initial dehydration reactor 10 is followed by a series of fixed bed catalytic reactors 11, 12, 13, 14 and 15 containing zeolite conversion catalyst. Inter-reactor coolers 10A, 11A, 12A, 13A, 14A and effluent cooler 15A control temperature of the process stream. Interstage separation means is provided for recovering water and hydrocarbons from the primary stage effluent stream. The first stage effluent is cooled to condense water and a major amount of $C_5+$ liquid hydrocarbons. These liquids are separated from the hydrocarbon vapor in phase separator means 16. By product water may be recovered from unreacted feedstock and discarded, or optionally a portion may be recycled, as indicated by the dashed lines. The liquid hydrocarbon phase and the ethene-rich light hydrocarbon vapor streams are recovered from separator 16. Optionally, unconverted DME may be removed by absorber 20. This optional section includes a compressor 19 and stripper 21. Other suitable fixed bed catalytic processes for conversion of methanol/DME to lower olefins are described in U.S. Pat. Nos. 4,387,263, 4,393,265, 4,361,715 and South African patent application Ref. No. V01750 (Clover et al) filed Mar. 30, 1983, the entire disclosures of which are incorporated herein by reference. While the primary stage dehydration reactor has been exemplified herein by a fixed bed unit, a suitable fluid catalyst apparatus is disclosed in U.S. Pat. No. 4,379,123 (Daviduk and Haddad).

A typical MTO operation is conducted over a fixed bed of small crystal (0.02–0.05μ) HZSM-5/alumina extrudate catalyst at about 170 kPa (25 psia), with a 1:1 $H_2O:CH_3OH$ equivalent ratio at 315° C. (600° F.) at a space velocity (WHSV=0.5–1) to convert about 50% of the oxygenated organic feedstock components to hydrocarbons. Table I lists the organic hydrocarbon product distribution from a typical MTO process.

TABLE I

| MTO Product Distribution | |
|---|---|
| Component | wt. % |
| Methane, wt. % | 0.6 |
| Ethylene, wt. % | 26.2 |
| Ethane, wt. % | 0.1 |
| Propylene, wt. % | 22.8 |
| Propane | 3.9 |
| Butenes | 7.9 |
| Isobutane | 3.9 |
| n-Butane | 2.6 |
| Pentenes | 2.4 |
| $C_5$ P + N | 7.1 |
| $C_6$ P + N | 5.1 |
| $C_7$ O | 0.6 |
| $C_7$ P + N | 3.2 |
| $C_7$ O | 0.7 |
| $C_8$ P + O + N | 2.1 |
| $C_9$ P + O + N | 1.3 |
| $C_{10}$ P + O + N | 1.1 |
| Benzene | 0.1 |
| Toluene | 0.5 |
| $C_8$ Aromatics | 3.5 |
| $C_9$ Aromatics | 2.1 |
| $C_{10}$ Aromatics | 2.2 |
| (Durene) | (1.7) |

Sorption Fractionation

The light hydrocarbon stream recovered from the primary conversion stage preferably contains a major amount of $C_2$–$C_4$ olefins. The novel system includes a first fractionation means for recovering ethene from the primary stage olefinic vapor including a sorption tower operatively connected to selectively sorb $C_3+$ hydrocarbons from the olefinic vapor in a liquid sorption stream. Since the interstage fractionation unit is usually operated at a pressure higher than the primary stage and lower than the secondary conversion stage, vapor compression means for the primary stage light hydrocarbon stream and means for pressurizing and heating the liquid sorption stream containing $C_3+$ sorbate are provided.

A suitable sorption fractionation system is described in copending U.S. patent appliation Ser. No. 508,779 filed June 29, 1983 (Hsia et al) now U.S. Pat. No. 4,479,812, the disclosure of which is incorporated herein by reference. The $C_2-$ and $C_3+$ separation is accomplished by a single absorber-stripper using gasoline recycle as absorbent and pumparounds for removing absorption heat. The amount of absorbent is set by the amount of recycle gasoline required in the $C_3+$ olefins conversion reaction thereby allowing the tower bottom stream to be pumped directly to the reactor pressure. Without using refrigeration, this tower efficiently and effectively separates the ethylene and light gases ($H_2$, CO, $CO_2$ and $CH_4$) from the $C_3+$ hydrocarbon.

The gasoline sorbent is an aliphatic hydrocarbon mixture boiling in the normal gasoline range of about 50° to 165° C. (125° to 330° F.), with minor amounts of $C_4$–$C_5$ alkanes and alkenes. Preferably, the total gasoline sorbent stream to feedstock weight ratio is greater than about 3:1; however, the content of $C_3+$ olefinic components in the feedstock is a more preferred measure of sorbate to sorbent ratio. Accordingly, the process may be operated with a mole ratio of about 0.2 moles to about 10 moles of gasoline per mole of $C_3+$ hydrocarbons in the feedstock, with optimum operation utilizing a sorbent:sorbate molar ratio about 1:1 to 1.5:1.

It is understood that the various process conditions are given for a continuous system operating at steady state, and that substantial variations in the process are possible within the inventive concept. In the detailed examples, metric units and parts by weight are employed unless otherwise specified.

Figure 3:
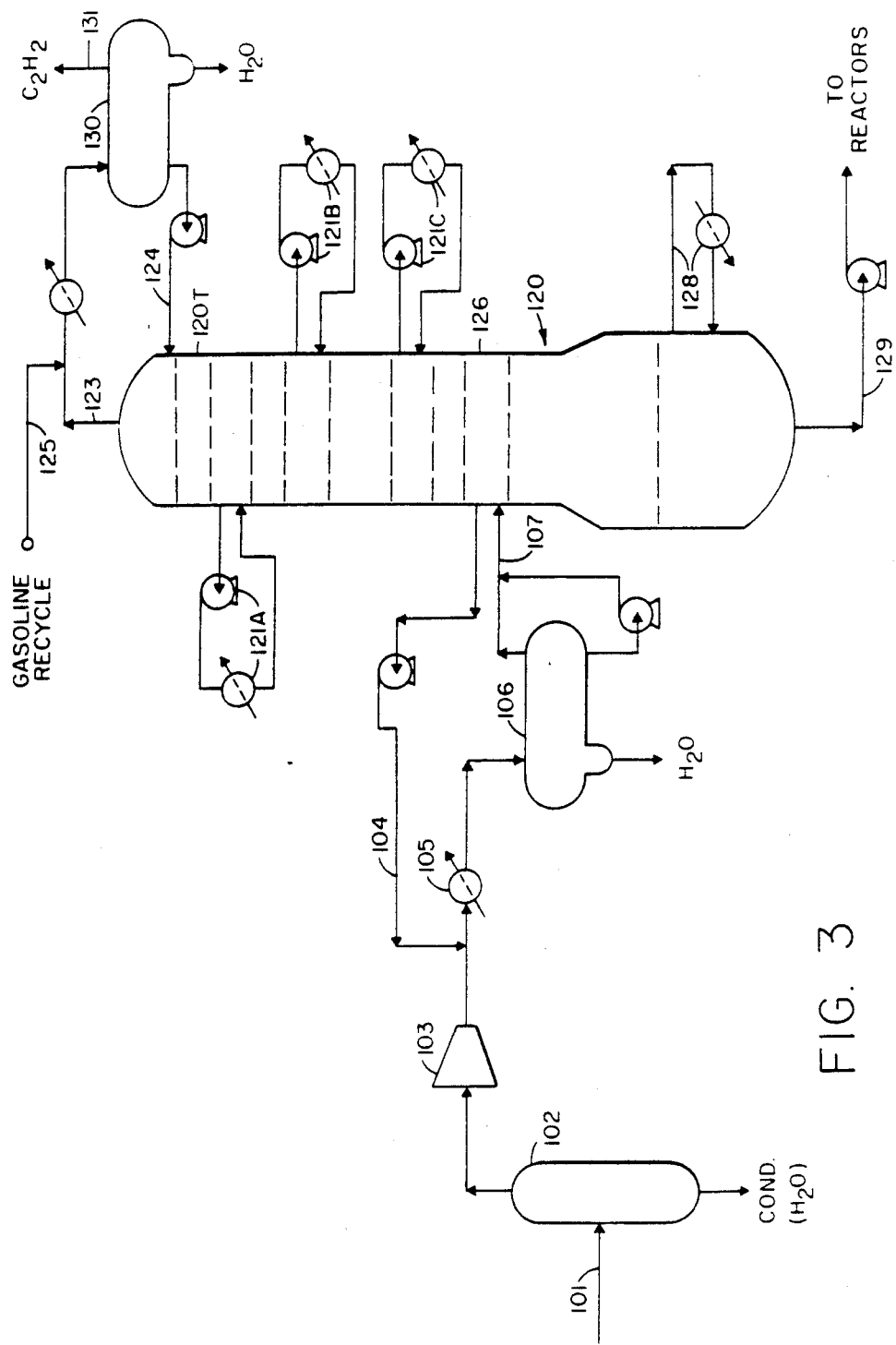
FIG. 3 is a preferred sorption fractionation and reactor system.

Referring to FIG. 3 of the drawing, olefinic feedstock is introduced to the system through a feedstock inlet 101, passing through knockout pot 102 to remove any condensate, such as water. At this point the vapor is at a temperature from ambient up to about 38° C. (100° F.) and a pressure of about 60 kPa (75 psig), and is pressurized by compressor means 103 to about 2230 kPa (310 psig). This pressurized stream is then mixed with a liquid downcomer stream 104 from fractionating tower 120, cooled in exchanger 105 to about 35°–40° C. and passed to phase separator 106 where condensed water is removed. The hydrocarbon stream is then fed via conduit 107 connected between stages of fractionating sorption tower 120 wherein gaseous olefinic feedstock is contacted with liquid sorbent in a vertical fractionation column operating at least in the upper portion thereof in countercurrent flow. Effectively this unit is a $C_2/C_3+$ splitter. The sorption tower employs a plate column; however, the fractionation equipment may employ vapor-liquid contact means of various designs in each stage including packed beds of Raschig rings, saddles or other porous solids or low pressure drop contact devices.

Sorption tower 120, as depicted, has multiple contact zones, with the heat of absorption being removed via interstage pump around cooling means 121A, B, and C. The liquid gasoline sorbent is introduced to the sorption tower through an upper inlet means 125 above the top contact section 120T. It is preferred to mix incoming liquid sorbent with outgoing splitter overhead ethylene-rich gas. High purity ethylene is recovered from the system through gas outlet 131 and sent to storage, further processing or conversion to other products. Liquid sorbent from separator 130 is then pumped to the upper liquid inlet 124 for countercurrent contact in a plate column or the like with upwardly flowing ethylene rich vapors. Liquid from the bottom of upper contact zone is pumped to a heat exchanger in loop 121A, cooled and returned to the tower, then cooled in loop 121B adjacent to an intermediate contact zone, again cooled in loop 121C, and returned to the tower above contact zone 126, which is located above the feedstock inlet 107. Under tower design conditions of about 2060 kPa (300 psia), it is preferred to maintain liquid temperature of streams entering the tower from 121, 107 and 124 at about 40° C. (100° F.). The lower contact zone provides further fractionation of the olefin-rich liquid. Heat is supplied to the sorption tower by removing liquid from the bottom via reboiler loop 128, heating this stream in a heat exchanger, and returning the reboiled bottom stream to the tower below contact zone 126. The liquid sorbate-sorbent mixture is withdrawn through bottom outlet 129 and pumped to storage or directly to the secondary stage for further reaction. The fractionator bottoms stream 129 is recovered at about 120° C. (250° F.), then pumped to the higher reactor pressure (e.g., about 4670 kPa, 665 psig) and passed to the secondary conversion stage. A typical sorption fractionation material balance is given below, for steady state operation using olefinic feed gas from the MTO primary stage. The units are expressed in moles per hour.

TABLE II

SORPTION FRACTIONATION MATERIAL BALANCE

| | FEED GAS | RECYCLE GASOLINE | GAS PRODUCT STREAM | LIQUID SORBATE STREAM |
|---|---|---|---|---|
| $H_2$ | 1.17 | — | 1.17 | — |
| CO | 0.22 | — | 0.22 | — |
| $CO_2$ | 0.38 | — | 0.38 | — |
| $C_1$ | 0.63 | — | 0.63 | — |
| $C_2=$ | 14.83 | — | 14.78 | 0.05 |
| $C_2$ | 0.11 | — | 0.10 | 0.01 |
| $C_3=$ | 8.09 | — | 0.36 | 7.73 |
| $C_3$ | 1.62 | — | 0.02 | 1.60 |
| $iC_4$ | 1.00 | 0.09 | 0.03 | 1.06 |
| $C_4=$ | 2.40 | 0.03 | 0.01 | 2.42 |
| $nC_4$ | 0.32 | 0.17 | 0.04 | 0.45 |
| $iC_5$ | 0.67 | 2.64 | 0.25 | 3.06 |
| $C_5$ | 0.24 | 1.23 | 0.11 | 1.36 |
| $nC_5$ | 0.06 | 0.22 | 0.02 | 0.26 |
| $C_6+$ | 0.81 | 11.19 | 0.13 | 11.87 |
| $H_2O$ | 0.37 | — | 0.03 | — |
| | 32.92 | 15.58 | 18.27 | 29.88 |

Distillate Mode

Oligomerization Reactor Operation

The main distillate production stage provides catalytic oligomerization reactor means containing medium pore shape selective zeolite oligomerization catalyst for converting olefinic hydrocarbons in the sorption stream to liquid hydrocarbons comprising a major amount of distillate. This process stream is passed to second fractionation means for separating secondary stage effluent into a light hydrocarbon stream rich in LPG ($C_3$-$C_4$) aliphatic hydrocarbons, a $C_5+$ gasoline stream and distillate range stream. Means is provided for recycling at least a portion of the $C_5+$ gasoline stream to the first sorption fractionation means as a lean sorbent stream.

Figure 4:
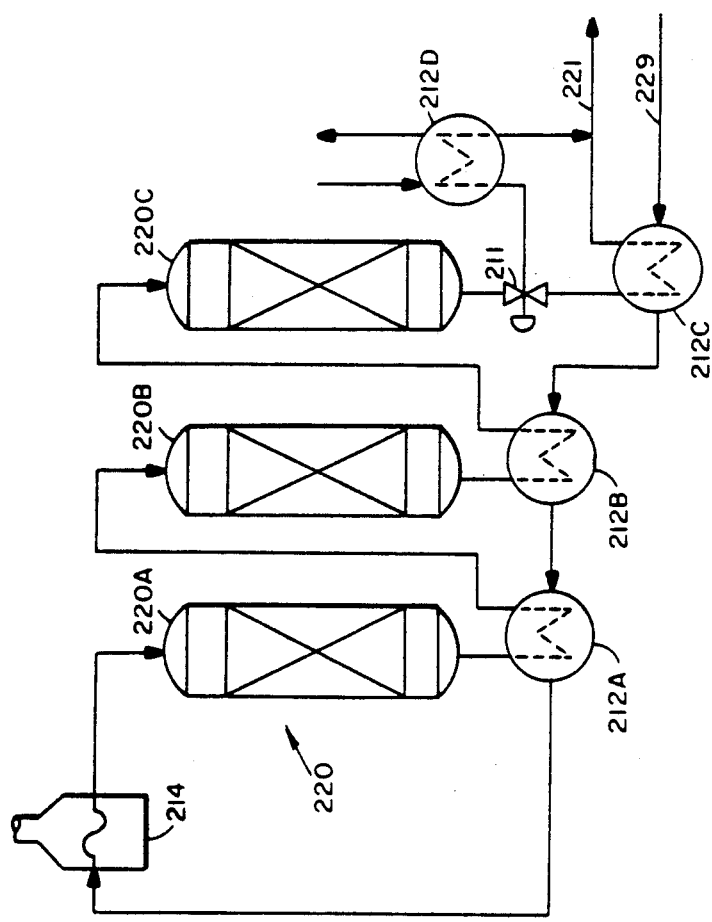
FIG. 4 is a typical olefin conversion reactor system for distillate mode operation.

A typical distillate mode secondary stage reactor system 220 is shown in FIG. 4. A plural reactor system may be employed with inter-reactor cooling, whereby the reaction exotherm can be carefully controlled to prevent excessive temperature above the normal moderate range of about 190° to 315° C. (375°–600° F.). The olefinic feedstream comprising the $C_3+$ light hydrocarbons and sorbent gasoline is introduced through conduit 229 and carried by a series of conduits through heat exchangers 212A, B, C and furnace 214 where the feedstream is heated to reaction temperature. The olefinic feedstream is then carried sequentially through a series of zeolite beds 220A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 1.5. The heat exchangers 212A and 212B provide inter-reactor cooling and 212C reduces the effluent to separation temperature. An optional heat exchanger 212D may further recover heat from the effluent stream 121 prior to separation.

Preferably, the secondary stage process conditions are optimized to produce heavy liquid hydrocarbons having a normal boiling above 165° C. (330° F.) are fed as a continuous stream to a final fractionator unit (such as a distillation system). Gasoline, rich in $C_5+$ olefins and lighter hydrocarbons are fractionated in a tower to provide an olefinic gasoline stream for recycle to the MOGD reactor system or recovered as product. The lighter hydrocarbons, rich in $C_3$-$C_4$ alkenes may be condensed and recovered as LPG product or optionally recycled to the MOGD reactor system. The secondary stage typical HZSM-5 fixed bed reactor system depicted in FIG. 4, operates at 0.6 liquid hourly space velocity (based on olefins fed to reactors), 1:1 gasoline-:olefin recycle ratio, temperature of 230° C. (450° F.) (SOC) to 315° C. (600° F.) (EOC) and a total pressure of 4225 kPa (600 psig) at minimum olefin partial pressure at the inlet of 1100 kPa (160 psig). The secondary stage effluent from such a typical system is shown below.

TABLE III

| Component | Wt. % |
|---|---|
| $CH_4$ | 0.07 |
| $C_2H_6$ | 0.13 |
| $C_3H_8$ | 2.80 |
| $IC_4H_{10}$ | 2.00 |
| $NC_4H_{10}$ | 2.00 |
| $i$-$C_5H_{12}$ | 0.42 |
| $n$-$C_5H_{12}$ | 0.03 |
| $C_5H_{10}$ | 0.95 |
| $C_6$-330° (Gasoline) | 12.60 |
| 330° + (Distillate) | 79.00 |

A typical product fractionation system is described in copending U.S. patent application Ser. No. 488,834 filed Apr. 26, 1983 (Owen et al) now U.S. Pat. No. 4,456,779, incorporated herein by reference.

It is within the inventive concept to cascade substantially all $C_3+$ vapor and liquid hydrocarbon product from the MTO stage into the distillate mode reactor followed by hydrotreating of the distillate product as depicted in FIG. 1. This will minimize the number of process steps and will maximize distillate production by polymerizing gasoline range olefins, and by alkylating gasoline range aromatics. Durene can be reduced via saturation to its corresponding naphthene in a subsequent mild hydrotreating step. Substantially all of the polymethylbenzenes or other aromatics formed in the dehydration reactor stage can be accumulated in the distillate fraction according to the present invention, and hydrotreated distillate durene content is decreased substantially below 2 wt. %, preferably below 1%.

The present process is particularly useful in producing a major product stream wherein the 165 C+ fraction consists mainly of $C_{10}$ to $C_{20}$ aliphatic hydrocarbons containing a minor amount of cyclic components. The low temperature, high pressure distillate mode secondary stage operation favors the formation of linear or slightly-branched oligomers.

High Severity Reactor Operation

Figure 5:
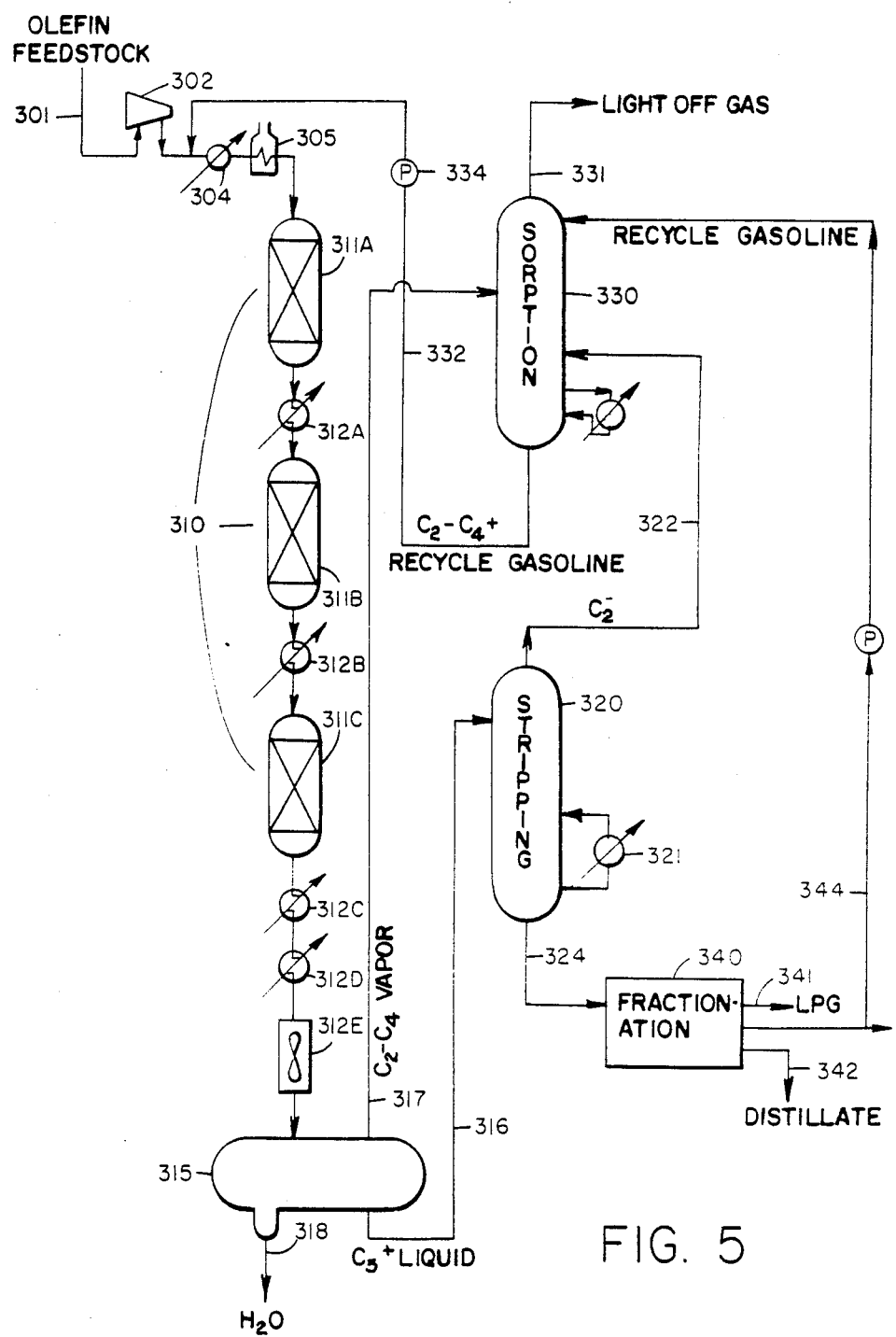
FIG. 5 is a process flow diagram for a high severity reactor system and effluent treatment system.

Referring to the FIG. 5 of the drawing, olefinic feedstock is supplied to the plant through fluid conduit 301 under steady stream conditions. This $C_{2+}$ feedstream is pressurized by compressor 302 and then sequentially heated by passing through process heat exchange unit 304 and furnace 305 to achieve the temperature for catalytic conversion in reactor system 310, including plural reactor vessels 311A, B, C, etc.

The reactor sub-system section shown consists of three downflow fixed bed, series reactors on line with heat exchanger cooling means 312 A, B, C, D, E between reactors and following the subsystem. The reactor configuration allows for any reactor to be in any position, A, B or C. The reactor in position A has the most aged catalyst and the reactor in position C has freshly regenerated catalyst. The cooled reactor effluent is first separated in a phase separator unit 315 is to provide a condensed $C_5{}^+$ hydrocarbon liquid stream 316 and an ethene-rich vapor stream 317 comprising $C_2$-$C_4$ aliphatic hydrocarbons, along with any other unreacted gaseous components which might be present in the feedstock, such as hydrogen, carbon oxides, methane, nitrogen or other inert gases. Extraneous water may be removed from the system through separator line 318.

Condensed hydrocarbon reactor effluent 316 separated from the effluent vapor is further fractionated. A stripping unit 320 which may be reboiled by exchanging a reactor effluent stream with tower bottoms in reboiler 321, removes a significant fraction of dissolved light gases, including a minor amount of unreacted ethene. The $C_2{}^-$ stripped gases are passed through conduit 322 operatively connecting the stripper with a downstream sorption unit 330. Ethane and heavier hydrocarbons are removed from the recycle loop through stripper 320. This tower may be designed to lose as little ethylene as possible while maintaining a reasonable tower bottom temperature. High pressure favors the split between ethylene and ethane. Preferably the liquid stripper effluent 324 is debutanized in a fractionation subsystem 340 to provide a $C_4{}^-$ overhead stream, which is deethanized to provide LPG ($C_3$-$C_4$ alkane) product 341 and light offgas. The $C_5{}^+$ debutanizer bottom stream is split in an atmospheric distillation tower to provide raw distillate product stream 342 and an olefinic gasoline stream 344 for recycle and/or recovery of a minor amount as raw gasoline product.

To recycle unconverted ethylene, recycle gasoline is used to selectively absorb it in the ethylene absorber 330. Ethylene is recovered from the vapor stream 317 leaving the reactor effluent separator and from the stripper overhead 322. The $H_2$, CO, $CO_2$ and $CH_4$ inerts which may enter with the feed are removed in the tower overhead via conduit 331 to prevent their build up in the system.

The gasoline sorbent is an aliphatic hydrocarbon mixture boiling in the normal gasoline range of about 50° to 165° C. (125° to 330° F.), with minor amounts of $C_4$-$C_5$ alkanes and alkenes. Preferably, the total gasoline sorbent stream to ethylene sorbate mole ratio is greater than about 4:1. The process may be operated with a mole ratio of about 0.2 moles to about 10 moles of gasoline per mole of $C_2{}^+$ olefins in the feedstock.

The tower pressure and bottom temperature may be selected such that enough $CO_2$ leaves the system without carrying too much ethylene with it. Ethylene absorption efficiency can be improved if $CO_2$ is removed by an optional amine scrubber or the like (not shown) before entering the tower.

There is no need for a recycle compressor because all the recovered ethylene is dissolved in the recycle gasoline as a sorbate stream 332 and passed by pump 334 to the reactor. Advantageously, the liquid recycle stream is brought to process pressure before being heated to vaporize at least a portion of the olefinic components.

It is understood that the various process conditions are given for a continuous system operating at steady state, and that substantial variations in the process are possible within the inventive concept. In the detailed examples, metric units and parts by weight are employed unless otherwise specified.

The fractionation towers depicted in the drawing may employ a plate column in the primary tower and a packed column in the secondary tower, however, the fractionation equipment may also employ vapor-liquid contact means of various designs in each stage including packed beds of Raschig rings, saddles or other porous solids or low pressure drop contact devices (Glitsch grids). The number of theoretical stages will be determined by the feedstream composition, liquid:vapor (L/V) ratios, desired recovery and product purity.

A typical high severity multi-zone reactor system employs inter-zone cooling, whereby the reaction exotherm can be carefully controlled to prevent excessive temperature above the normal moderate range of about 260° to 370° C.

Advantageously, the maximum temperature differential across any one reactor is about 30° C. ($\Delta T \sim 50°$ F.) and the space velocity (LHSV based on olefin feed) is about 0.5 to 1. Heat exchangers provide inter-reactor cooling and reduce the effluent to fractionation temperature. It is an important aspect of energy conservation in the MOGD system to utilize at least a portion of the reactor exotherm heat value by exchanging hot reactor effluent from one or more reactors with a fractionator stream to vaporize a liquid hydrocarbon distillation tower stream, such as the debutanizer bottoms. Optional heat exchangers may recover heat from the effluent stream prior to fractionation. Gasoline from the recycle conduit is pressurized by pump means and combined with feedstock, preferably at a mole ratio of about 2-3 moles per mole of olefin in the feedstock. It is preferred to operate the high severity reactors at elevated pressure of about 4200 to 7000 kPa (600-1000 psig), with a minimum olefin partial pressure of 1200 kPa at the reactor system inlet.

The reactor system contains multiple downflow adiabatic catalytic zones in each reactor vessel. The liquid hourly space velocity (based on total fresh feedstock) is about 1 LHSV. In this mode the molar recycle ratio for gasoline is at least equimolar, based on total olefins in the fresh feedstock and recycle. The preferred molar ratio olefinic gasoline to fresh feedstock olefin is at least 2:1. This will also assure adequate sorbent for the sorption unit. Typical reactor conditions are set forth in the following tables.

TABLE IV

| HIGH SEVERITY REACTOR SYSTEM | | | |
|---|---|---|---|
| Feedstock | | Yield on Olefin Converted | |
| Component | Wt % | Component | Wt % |
| Inerts | 5.00 | $CH_4$ | 0.10 |
| $CH_4$ | 2.00 | $C_2H_6$ | 3.90 |
| $C_2H_4$ | 81.20 | $C_3H_8$ | 4.00 |
| $C_2H_6$ | 0.62 | $IC_4H_{10}$ | 2.00 |
| $C_3H_6$ | 3.71 | $NC_4H_{10}$ | 2.00 |
| $C_3H_8$ | 0.20 | $IC_5H_{12}$ | 1.32 |
| $IC_4H_{10}$ | 0.25 | $NC_5H_{12}$ | 0.09 |
| $NC_4H_{10}$ | 0.45 | $C_5H_{10}$ | 2.99 |
| $C_4H_8$ | 0.12 | $C_6$-300° Gaso. | 39.60 |
| $IC_5H_{12}$ | 2.31 | 330° + Dist. | 44.00 |
| $NC_5H_{12}$ | 0.10 | | |

TABLE IV-continued

| HIGH SEVERITY REACTOR SYSTEM | |
|---|---|
| $C_5H_{10}$ | 1.73 |
| $C_6+$ | 2.31 |

| Conversion on Feed to Reactor | |
|---|---|
| Olefins | Wt. % |
| $C_2$ | 75 |
| $C_3$ | 95 |
| $C_4$ | 85 |

TABLE V
REACTOR CONDITIONS

| | |
|---|---|
| Space Velocity, LHSV (Based on olefins fed to reactor) | 0.5 |
| Reactor A inlet pressure, psig | 900 |
| Minimum Olefin pp at reactor inlet, psia | 180 |
| Exothermic Heat of Reaction BTU/# olefins converted | 1040 |
| Rate of Heat Release | Uniformly over bed |
| Maximum Allowable ΔT in Reactor, ° F. | 50 |
| Reactor Inlet Temperature SOC/EOC | 500/700° F. |
| Gasoline Recycle, Mol/Mol Olefin Feed | 2:1 |
| Coke on Catalyst, wt. % SOC | 0 |
| EOC | 30 |
| Cycle Length, Days | 30 |
| Catalyst | HZSM-5 1/16" Extrudate |

More than 90% of ethylene is recovered in the above example from the effluent.

While the invention has been described by specific examples and embodiments, there is no intent to limit the inventive concept except as set forth in the following claims.

We claim:

1. A multi-stage system for converting olefins to heavier hydrocarbons comprising sorption prefractionation means for separating olefinic feedstock into a sorbate stream rich in liquified olefins and a vapor stream rich in light olefins;

first stage catalytic reactor means for oligomerizing said olefins from the sorbate stream including means for maintaining the first stage at elevated pressure and predetermined temperature for producing substantially linear aliphatic hydrocarbons;

second stage catalytic reactor means for oligomerizing said light olefins from the vapor stream including means for maintaining the second stage under high severity conditions at substantially higher temperature than the first stage;

product fractionation means for separating combined effluent from the first and second stages to separate and recover heavy hydrocarbon product and a sorbent recycle fraction; and means for recycling said sorbent fraction to the sorption prefractionation means and means for contacting olefinic feedstock with the recycled sorbent.

2. A continuous catalytic system for converting olefinic feedstock comprising ethylene and $C_3+$ olefins to heavier liquid hydrocarbon product comprising, in combination:

feedstock sorption means for prefractionating the olefinic feedstock to obtain a gaseous stream rich in ethylene and a liquid stream containing $C_3+$ olefin;

primary stage reactor means for contacting the liquid stream from the prefractionating sorption means with shape selective medium pore zeolite oligomerization catalyst in a distillate mode catalytic reactor zone at elevated temperature and pressure to provide a heavier hydrocarbon effluent stream comprising distillate, gasoline and lighter hydrocarbons;

means for fractionating the effluent stream to recover distillate, gasoline and lighter hydrocarbons;

means for recycling at least a portion of the recovered gasoline as a first liquid sorbent stream sequentially to the prefractionating sorption means and to the primary stage reactor means;

means for combining said ethylene-rich gaseous stream from the sorption means with a liquid hydrocarbon stream containing heavier liquid hydrocarbons;

secondary stage reactor means for contacting the combined ethylene-rich stream at elevated temperature and pressure in a high severity reaction zone with shape selective medium pore zeolite oligomerization catalyst to convert at least a portion of the olefinic components to heavier hydrocarbons;

means for cooling secondary stage effluent to condense at least a portion of said heavier hydrocarbons;

means for separating the cooled and partially condensed secondary stage effluent stream into a vapor stream comprising unreacted light olefin and a condensed liquid hydrocarbon stream;

means for fractionating said condensed liquid hydrocarbons to provide a second liquid recycle sorbent stream and at least one product hydrocarbon stream;

means for contacting the cooled secondary stage effluent vapor stream under sorption pressure conditions with cooled recycle sorbent stream to sorb said unreacted light olefin into the second sorbent stream; and means for recycling the second sorbent stream rich in olefin for further conversion with said olefinic feedstock in the secondary stage reactor means.

3. The system of claim 2 wherein the recycled sorbent to each stage comprises $C_5+$ olefinic components produced by a common fractionation system.

4. The system of claim 2 wherein oligomerization catalyst in both stages comprises a shape-selective medium pore crystalline aluminosilicate zeolite having a silica:alumina mole ratio of at least 12 and a constraint index of about 1 to 12.

5. The system of claim 4 wherein the catalyst comprises HZSM-5 having an acid cracking activity of about 160 to 200.

6. A catalytic conversion system for upgrading lower olefins to produce heavier hydrocarbons including higher boiling range product, comprising in combination:

feedstock sorption means for prefractionating the lower olefins to produce a light olefinic vapor stream and a liquid olefinic stream comprising intermediate range hydrocarbon sorbent and lower olefinic sorbate;

means for pressurizing and heating the liquid olefinic stream to primary stage process conditions;

primary stage reactor means for contacting the intermediate range hydrocarbons under moderate process temperature conditions at high pressure with oligomerization catalyst to convert at least a portion of the olefinic hydrocarbons to intermediate and heavy hydrocarbon product;

secondary stage reactor means for contacting at least a portion of the light olefinic vapor stream with oligomerization catalyst under severe process temperature conditions to convert a major portion of the secondary stage feed stream to heavier hydrocarbons rich in intermediate range hydrocarbons;

fractionation means for recovering heavy product and intermediate range liquid hydrocarbons from the primary and/or secondary stage effluent; and means operatively connected between the product fractionation means and prefractionating means for recycling at least a portion of the intermediate range liquid hydrocarbons rich in olefinic hydrocarbons as a liquid sorbent stream.

7. The system of claim 6 wherein the primary and secondary stage reactor means each contain zeolite catalyst comprising a crystalline aluminosilicate having a silica:alumina ratio of at least 12 and a constraint index of about 1 to 12.

* * * * *